(12) United States Patent
Martinez et al.

(10) Patent No.: US 11,448,726 B2
(45) Date of Patent: Sep. 20, 2022

(54) SYSTEM AND METHOD FOR PRESENCE AND PULSE DETECTION FROM WIRELESS SIGNALS

(71) Applicant: Aerial Technologies Inc., Montreal (CA)

(72) Inventors: Michel Allegue Martinez, Terrebonne (CA); Negar Ghourchian, Montreal (CA); David Grant, Santa Rosa Valley, CA (US); Francois Morel, Kirkland (CA); Pauline Tranchant, Montreal (CA); Amir Minayi Jalil, Verdun (CA)

(73) Assignee: Aerial Technologies Inc., Montreal (CA)

( * ) Notice: Subject to any disclaimer, the term of this patent is extended or adjusted under 35 U.S.C. 154(b) by 0 days.

(21) Appl. No.: 17/006,579

(22) Filed: Aug. 28, 2020

(65) Prior Publication Data

US 2021/0063537 A1   Mar. 4, 2021

Related U.S. Application Data

(60) Provisional application No. 62/897,222, filed on Sep. 6, 2019, provisional application No. 62/893,109, filed on Aug. 28, 2019.

(51) Int. Cl.
*G08B 21/02* (2006.01)
*G01S 7/41* (2006.01)
(Continued)

(52) U.S. Cl.
CPC ............. *G01S 7/415* (2013.01); *G01S 7/006* (2013.01); *G01S 13/003* (2013.01);
(Continued)

(58) Field of Classification Search
CPC ....................................................... G01S 7/415
See application file for complete search history.

(56) References Cited

U.S. PATENT DOCUMENTS

| 8,073,441 | B1 | 12/2011 | Unger et al. |
| 8,461,988 | B2 * | 6/2013 | Tran ..................... A61B 5/0006 340/3.1 |

(Continued)

FOREIGN PATENT DOCUMENTS

| CA | 3044480 | 5/2018 |
| CN | 105828289 | 8/2016 |

(Continued)

OTHER PUBLICATIONS

PCT/IB2020/051503, Handling Concept Drift in Wi-Fi Based Localization, Feb. 22, 2020.

(Continued)

*Primary Examiner* — Qutbuddin Ghulamali
(74) *Attorney, Agent, or Firm* — Polsinelli LLP

(57) ABSTRACT

Systems and methods for detecting and monitoring human breathing, respiration, and heart rate using statistics about the wireless channel between two or more connected devices. A user is monitored for identifying patterns in the user's behavior that may allow the system to alert a caregiver to deviations in the user behavior that may be indicative of a potential issue, such as depression. A presence may further detected in a sensing area through the detection of spectral components in the breathing frequency range of comprises user includes transforming phase difference between spatial streams and amplitude of the samples representing frequency response of the channel for any frequency value into frequency domain to perform frequency analysis. Statistical analysis may be performed on the frequency space provided by the transformation. Micro motions may also be detected by detecting presence in a (Continued)

sensing area through the detection of spectral components in the micro motion frequency range.

16 Claims, 10 Drawing Sheets

(51) Int. Cl.
*G01S 7/00* (2006.01)
*G01S 13/88* (2006.01)
*G01S 13/00* (2006.01)
*G08B 21/18* (2006.01)

(52) U.S. Cl.
CPC ............ *G01S 13/886* (2013.01); *G08B 21/02* (2013.01); *G08B 21/182* (2013.01)

(56) References Cited

U.S. PATENT DOCUMENTS

| | | |
|---|---|---|
| 9,219,790 B1 | 12/2015 | Filev et al. |
| 9,414,115 B1 | 8/2016 | Mao et al. |
| 9,854,292 B1 | 12/2017 | Matthews et al. |
| 9,867,548 B2 | 1/2018 | Le et al. |
| 10,045,191 B2 | 8/2018 | Nguyen et al. |
| 10,419,880 B1 | 9/2019 | Long et al. |
| 10,818,384 B1 | 10/2020 | Peterson et al. |
| 10,999,705 B2 | 5/2021 | Martinez |
| 11,082,109 B2 | 8/2021 | Martinez |
| 11,218,769 B2 | 1/2022 | Martinez |
| 2002/0188668 A1 | 12/2002 | Jeffery et al. |
| 2006/0224938 A1 | 10/2006 | Fikes et al. |
| 2007/0024580 A1 | 2/2007 | Sands et al. |
| 2007/0266395 A1 | 11/2007 | Lee et al. |
| 2008/0262909 A1 | 10/2008 | Li et al. |
| 2010/0242063 A1 | 9/2010 | Slaney et al. |
| 2011/0029277 A1 | 2/2011 | Chowdhary et al. |
| 2011/0117924 A1 | 5/2011 | Brunner et al. |
| 2011/0129047 A1 | 6/2011 | Mashino et al. |
| 2011/0258039 A1 | 10/2011 | Patwa et al. |
| 2012/0053472 A1 | 3/2012 | Tran |
| 2012/0135733 A1 | 5/2012 | Cormier et al. |
| 2012/0324494 A1 | 12/2012 | Burger et al. |
| 2013/0014136 A1 | 1/2013 | Bhatia et al. |
| 2013/0102256 A1 | 4/2013 | Cendrillon et al. |
| 2013/0115974 A1 | 5/2013 | Lee et al. |
| 2014/0033240 A1 | 1/2014 | Card et al. |
| 2014/0223467 A1 | 8/2014 | Hayton et al. |
| 2014/0278389 A1 | 9/2014 | Zurek et al. |
| 2014/0358012 A1 | 12/2014 | Richards et al. |
| 2015/0026708 A1 | 1/2015 | Ahmed et al. |
| 2015/0050923 A1 | 2/2015 | Tu et al. |
| 2015/0092747 A1 | 4/2015 | Ganesan |
| 2015/0113556 A1 | 4/2015 | Weast et al. |
| 2015/0365787 A1 | 12/2015 | Farrell |
| 2016/0105700 A1* | 4/2016 | Collins .............. H04N 21/4126 725/14 |
| 2016/0127766 A1 | 5/2016 | Luk et al. |
| 2016/0174185 A1 | 6/2016 | Ramakrishnan et al. |
| 2016/0277529 A1 | 9/2016 | Chen et al. |
| 2016/0337701 A1 | 11/2016 | Khare et al. |
| 2016/0344779 A1 | 11/2016 | Jain et al. |
| 2017/0032191 A1 | 2/2017 | Ackland |
| 2017/0068790 A1 | 3/2017 | Fuerst |
| 2017/0135635 A1 | 5/2017 | Bostick et al. |
| 2017/0160089 A1 | 6/2017 | Jang et al. |
| 2017/0332192 A1 | 11/2017 | Edge |
| 2017/0354349 A1 | 12/2017 | Mohapatra et al. |
| 2017/0366955 A1 | 12/2017 | Edge |
| 2018/0008207 A1 | 1/2018 | Sarkela et al. |
| 2018/0181094 A1 | 6/2018 | Funk et al. |
| 2018/0184165 A1 | 6/2018 | Maughan et al. |
| 2018/0330406 A1 | 11/2018 | Deluca et al. |
| 2019/0051342 A1 | 2/2019 | Wootton et al. |
| 2019/0174170 A1 | 6/2019 | Chen |
| 2019/0178980 A1 | 6/2019 | Zhang et al. |
| 2019/0188756 A1 | 6/2019 | Bradley et al. |
| 2019/0306023 A1 | 10/2019 | Vasseur et al. |
| 2020/0036592 A1 | 1/2020 | Kholaif |
| 2020/0090022 A1 | 3/2020 | Ma et al. |
| 2020/0112939 A1* | 4/2020 | Scharf .................. H04L 43/0829 |
| 2020/0186321 A1 | 6/2020 | Hwang et al. |
| 2020/0226388 A1 | 7/2020 | Ghessassi |
| 2020/0265700 A1* | 8/2020 | Bergman ............. G08B 25/016 |
| 2020/0292572 A1 | 9/2020 | Bateni |
| 2020/0296463 A1 | 9/2020 | Martinez |
| 2020/0302478 A1 | 9/2020 | Martinez |
| 2020/0303046 A1 | 9/2020 | Martinez |
| 2020/0327430 A1 | 10/2020 | Martinez |
| 2020/0328793 A1 | 10/2020 | Martinez |
| 2020/0329343 A1 | 10/2020 | Martinez |
| 2020/0383119 A1 | 12/2020 | Sun et al. |
| 2020/0397365 A1 | 12/2020 | Zhang et al. |
| 2021/0120370 A1 | 4/2021 | Martinez |
| 2021/0352441 A1 | 11/2021 | Liu |
| 2022/0060234 A1 | 2/2022 | Martinez |
| 2022/0070633 A1 | 3/2022 | Ghoshal |
| 2022/0167050 A1 | 5/2022 | Martinez |

FOREIGN PATENT DOCUMENTS

| | | |
|---|---|---|
| WO | WO 2016/187458 | 11/2016 |
| WO | WO 2018/094502 | 5/2018 |
| WO | WO 2020/170221 | 8/2020 |
| WO | WO 2020/240526 | 12/2020 |
| WO | WO 2021/084519 | 5/2021 |

OTHER PUBLICATIONS

U.S. Appl. No. 16/796,662, Michel A. Martinez, Smart Media Display, filed Feb. 20, 2020.
U.S. Appl. No. 16/795,195, Michel A. Martinez, Advertisement Engagement Measurement, filed Feb. 19, 2020.
U.S. Appl. No. 16/798,138, Michel A. Martinez, Small Motion Vector Identification in a Wi-Fi Motion Detection System, filed Feb. 21, 2020.
U.S. Appl. No. 16/794,668, Michel A. Martinez, Robotic H Matrix Creation, filed Feb. 19, 2020.
U.S. Appl. No. 16/798,319, Michel A. Martinez, Wi-Fi Based Condition Monitoring, filed Feb. 22, 2020.
U.S. Appl. No. 16/795,219, Michel A. Martinez, Self-Learning Based on Wi-Fi-Based Monitoring and Augmentation, filed Feb. 19, 2020.
U.S. Appl. No. 16/798,148, Seyedehsan Bateni, Wireless Motion Detection Using Multiband Filters, filed Feb. 21, 2020.
PCT Application No. PCT/IB2020/051503 International Preliminary Report on Patentability dated Aug. 10, 2021.
U.S. Appl. No. 16/798,148 Office Action dated Oct. 22, 2021.
Deng et al., "CC-DTW: An Accurate Indoor Fingerprinting Localization Using Calibrated Channel State Information and Modified Dynamic Time Warping", Sensors 19, No. 9:1984, Apr. 28, 2019 (Apr. 28, 2019), [online] [retrieved on Aug. 20, 2020 (Aug. 20, 2020)], Retrieved from the internet: https://www.mdpif.com/1424-8220/19/9/1984.
Ghourchian et al., "Real-Time Indoor Localization in Smart Homes Using Semi-Supervised Learning", Association for the Advancement of Artificial Intelligence, Twenty-Ninth AAAI Conference on Innovative Applications, pp. 4670-4677, Feb. 8, 2017 (Aug. 2, 2017), [online] [retrieved on Aug. 20, 2020 (Aug. 20, 2020)], Retrieved from the internet: https://aaai.org/ocs/index.php/IAAI/IAAI17/paer/view/15010.
Rui Zhou et al., "Device-free Localization Based on CSI Fingerprints and Deep Neural Networks", 15 Annual IEEE International Conference on Sensing, Communication, and Networking (SECON), Jun. 11, 2018 (Jun. 11, 2018), [online] [retrieved on Aug. 20, 2020 (Aug. 20, 2020] Retrieved from the internet: https://dl.acm.org/doi/10.1145/2639108.2639143.
Xuyu Wang et al., "CSI-Based Fingerprinting for Indoor Localization: A Deep Learning Approach", IEEE Transactions on Vehicular Technology, vol. 66, No. 1, pp. 763-776, Mar. 22, 2016 (Mar. 22,

(56) References Cited

OTHER PUBLICATIONS

2016), [online] [retrieved on Aug. 20, 2020 (Aug. 20, 2020), Retrieved from the internet: https://ieeexplore://ieeexplore.ieee.org/documents/7438932.

Yang Wang et al., "E-eyes: Device-free Location-oriented Activity Identification Using Fine-grained Wifi Signatures", MobiCom'14, pp. 617-628 Sep. 7, 2014 (Sep. 7, 2014), [retrieved on Aug. 20, 2020 (Aug. 20, 2020)], Retrieved from the internet: https://dl.acm.org/doi/10.1145/2639108.2639143.

PCT Application No. PCT/IB2020/055186 International Search Report and Written Opinion dated Oct. 15, 2020.

U.S. Appl. No. 17/392,678, Michel A. Martinez, Self-Learning Based on Wi-Fi Based Monitoring and Augmentation, filed Aug. 3, 2021.

U.S. Appl. No. 16/798,148 Office Action datd Oct. 22, 2021.

PCT Application No. PCT/IB2020/060271 International Search Report and Written Opinion dated Feb. 15, 2021.

U.S. Appl. No. 16/796,662 Office Action dated Feb. 12, 2021.

U.S. Appl. No. 17/131,078, Michel A. Martinez, Monitoring Activity Using Wi-Fi Motion Detection, filed Dec. 22, 2020.

PCT Application No. PCT/IB2020/051503 International Search Report and Written Opinion dated Jul. 30, 2020.

U.S. Appl. No. 16/798,138 Office Action ated Sep. 8, 2020.

U.S. Appl. No. 16/798,148 Final Office Action dated Apr. 8, 2022.

U.S. Appl. No. 17/131,078 Non- Final Office Action dated Mar. 2, 2022.

PCT Application No. PCT/IB2020/055186 International Preliminary Report on Patentability dated Nov. 16, 2021.

U.S. Appl. No. 16/795,198 Office Action dated Jan. 25, 2022.

U.S. Appl. No. 16/798,319 Office Action dated Dec. 29, 2021.

PCT Application No. PCT/IB2020/060271 International Preliminary Report on Patentability dated May 3, 2022.

U.S. Appl. No. 16/794,668 Office Action dated May 24, 2022.

U.S. Appl. No. 16/798,319 Final Office Action dated Jun. 13, 2022.

U.S. Appl. No. 16/798,148 Office Action dated Jul. 26, 2022.

\* cited by examiner

SYSTEM AND METHOD FOR PRESENCE AND PULSE DETECTION FROM WIRELESS SIGNALS

CROSS-REFERENCED TO RELATED APPLICATIONS

The present patent application claims the priority benefit of U.S. provisional application No. 62/893,109 filed Aug. 28, 2019 and U.S. provisional application No. 62/897,222 filed Sep. 6, 2019, the disclosures of which are incorporated by reference herein.

BACKGROUND OF THE INVENTION

1. Field of the Invention

The present disclosure is generally related to motion and activity detection using Wi-Fi or a radio signal.

2. Description of the Related Art

Motion detection is the process for detecting a change in the position of a user relative to its surroundings. Motion detection can be accomplished by a software-based monitoring algorithm. A motion detection system can analyze the type of motion to see if an alarm is warranted. Wi-Fi localization refers to translating observed Wi-Fi signal strengths into locations.

Wi-Fi-based systems should be able to detect if a user is present in the environment even when no displacement or limb movement is produced. One solution is to use the periodic distortions caused by chest and lung breathing motion. Fine-grained channel state information (CSI) provided by pairs of Wi-Fi devices have been used to measure breathing rates, by analyzing time series in time and frequency domains often with an estimation error below one breathing cycle per minute. Detecting the effects of the respiration of a human being is desirable and can be used for presence detection and/or health monitoring. There is a need in the art for passive monitoring of human respiration from CSI.

SUMMARY OF THE CLAIMED INVENTION

The present disclosure includes systems and methods that use a pair of connected devices in a sensing area to detect whether there is user presence and estimate the user's breathing rate in the frequency domain. Detection of movement or no movement occurs using passive Wi-Fi or radio signals. Biorhythm, such as heart rate and respiration, is also detected and used as a source of positioning and localization. Activity data and engagement level data associated with the user are stored for a plurality of time periods. One or more time periods are identified where the stored user activity data and the stored engagement level data are correlated. Current activity data and current engagement level data are compared to identify one or more cycles. When there is a deviation in the cycles, an alert score is incremented and once the alert score is above a threshold, an alert is sent to a device associated with the user.

BRIEF DESCRIPTIONS OF THE DRAWINGS

DETAILED DESCRIPTION

Systems and methods are provided for detecting and monitoring human breathing using statistics about the wireless channel between two or more connected devices, and more particularly for detecting of various levels of breathing, respiration, and heart rate for pulse detection of a user within the Wi-Fi range. Further embodiments include methods for detecting presence in a sensing area through the detection of spectral components in the breathing frequency range of beings, as well as for transforming phase difference between spatial streams and amplitude of the samples representing frequency response of the channel for any frequency value into frequency domain to perform frequency analysis; and performing statistical analysis on the frequency space provided by the transformation. Further, micro motions may be detected by detecting presence in a sensing area through the detection of spectral components in the micro motion frequency range. Some embodiments may include systems for sensing breathing of a human using a Wi-Fi motion detection.

Figure 1:
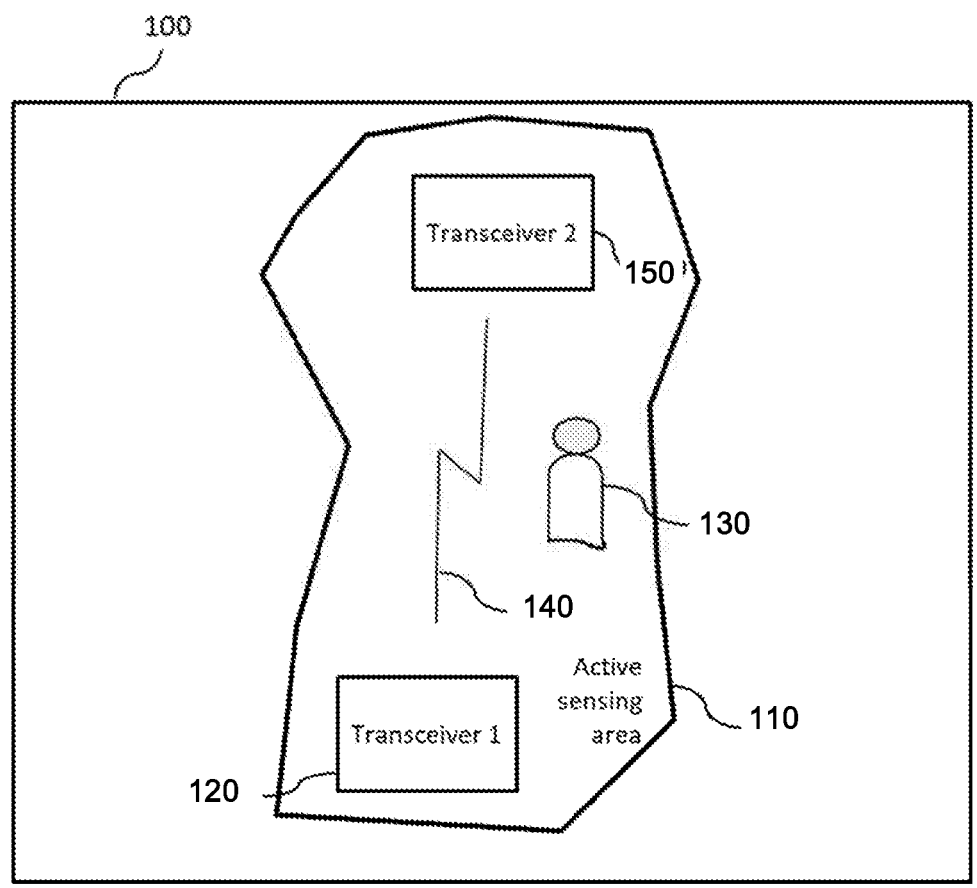
FIG. 1 illustrates a system able to sense objects within a sensing area via wireless signals.

FIG. 1 illustrates a systems for detecting presence and/or estimate the breathing rate of a user 130 while analyzing information about the state of the wireless channel between two connected devices 120 (transceiver 1) and 150 (transceiver 2), independently from the particular network topology in which these devices are associated. An example can be an access point (AP) connected to a client station (STA) such as a Wi-Fi-enabled TV in IEEE 802.11n and/or IEEE 802.11 ac. The wireless link between the devices 120 and 150 is represented by 140, where the state of the channel, frequency and phase responses, are estimated accordingly to the standard IEEE 802.11n and/or IEEE 802.11 ac. This information is reported as CSI data. The effective area where the state of the wireless channel can be estimated is 110. The area 100 is any space that belongs to any type of building where the frequency response and phase response of the channel can be estimated.

A statistical approach for channel frequency response that uses distortions caused by the chest, lung, abdomen and other body parts breathing movements of a user 130 is implemented to estimate breathing rate. In order to demonstrate the effectiveness of the proposed method, an example of the measured breathing rate is described herein. This approach allows estimating the breathing of a user even though the user is not in the direct path between the two devices that are connected exchanging/estimating the frequency and phase responses of the wireless channel between the devices.

Figure 2:
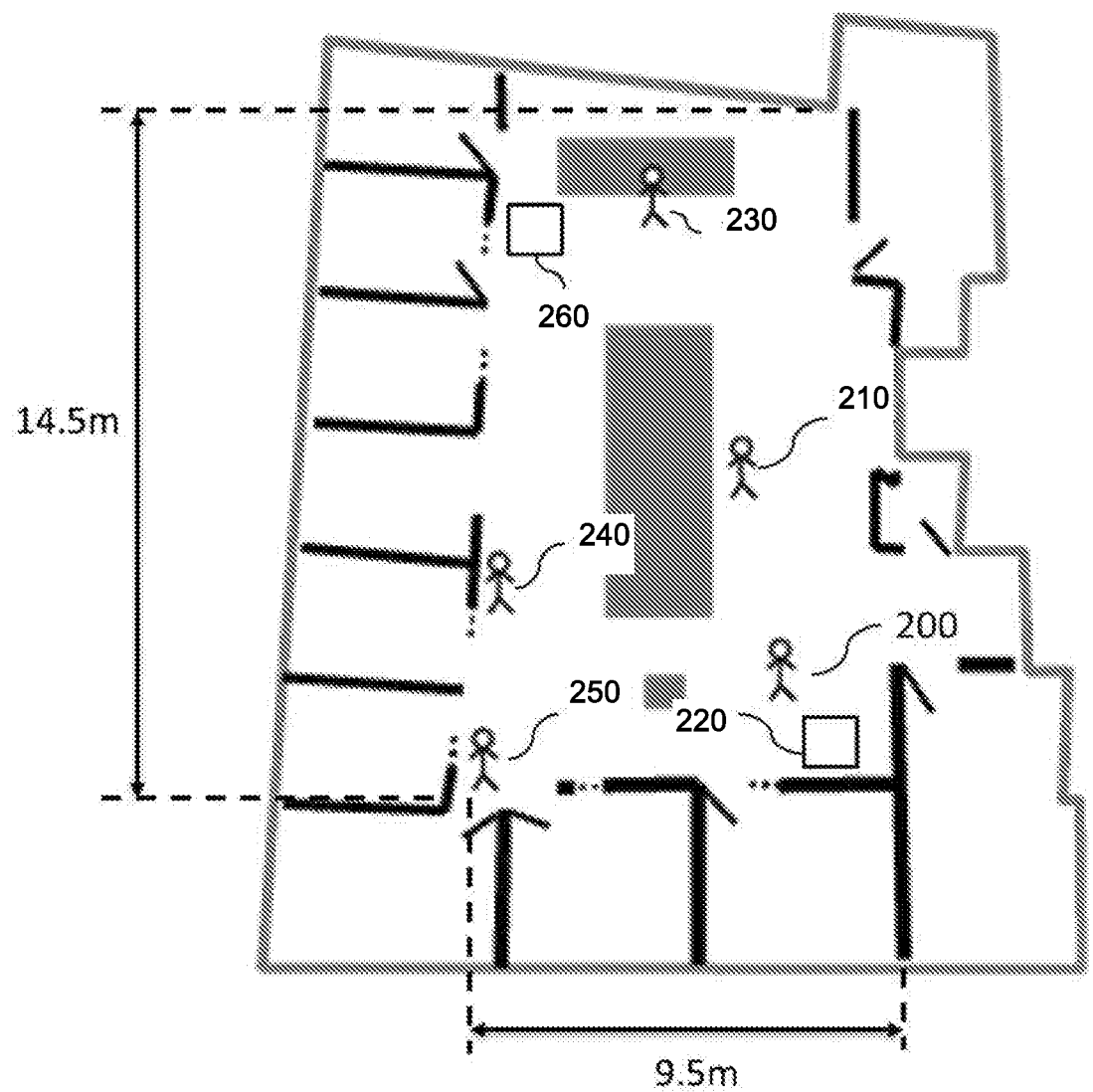
FIG. 2 illustrates a test case scenario which can be considered a large space used to exhibit the capabilities and efficiency of the methods proposed herein.

As an example, two Wi-Fi-enabled devices following IEEE 802.11ac standard 220 and 260 were used as illustrated in FIG. 2. In the channel estimation process, one device acts as a transmitter and the other one as a receiver, in a N_tx×N_rx multiple input multiple output (MIMO) system with N_tx transmitting antennas and N_rx receiving antennas. The Wi-Fi signal propagates between the transmitter and receiver through multiple spatial streams using Orthogonal Frequency Division Multiplexing (OFDM). In this example, used to demonstrate the approach proposed herein, CSI can be obtained at device 220 and/or 260. A sampling rate of 33.33 Hz, which is low compared to the state-of-the-art approaches, was fixed by using an echo command in 220, which generates traffic in the link between devices 220 and 260 making possible the estimation of the frequency response and phase response of the channel reported as CSI data. This sampling rate is used as an example and shall not limit the scope of the present approach. CSI characterizes the signal propagation between 220 and 260, and provides information on signal distortions such as attenuation, scattering, reflections, that are caused by the configuration of the environment and human motion interacting with the wireless signal used by devices 220 and 260.

Devices 220 and 260 were placed 12 meters away from each other in a large room, with tables, desks, computers and other little objects in between the devices. FIG. 2 depicts device placement (220, 260) and floor plan of the environment setup. Several metadata files containing CSI information were captured. In the breathing condition a user was breathing in a steady and controlled fashion, matching the inhale-exhale pace to an auditory metronome. The user was staying still at several locations in the environment indicated by 200, 210, 230, 240 or 250. At each location, the user was either lying down on the ground or sitting still on a chair. The same number of captures was taken in each position, sitting or lying. Additional captures were performed when nobody was present in the environment, which generates the baseline condition in order to compare signals in the breathing condition, and signals with no one within the sensing area.

Figure 3:
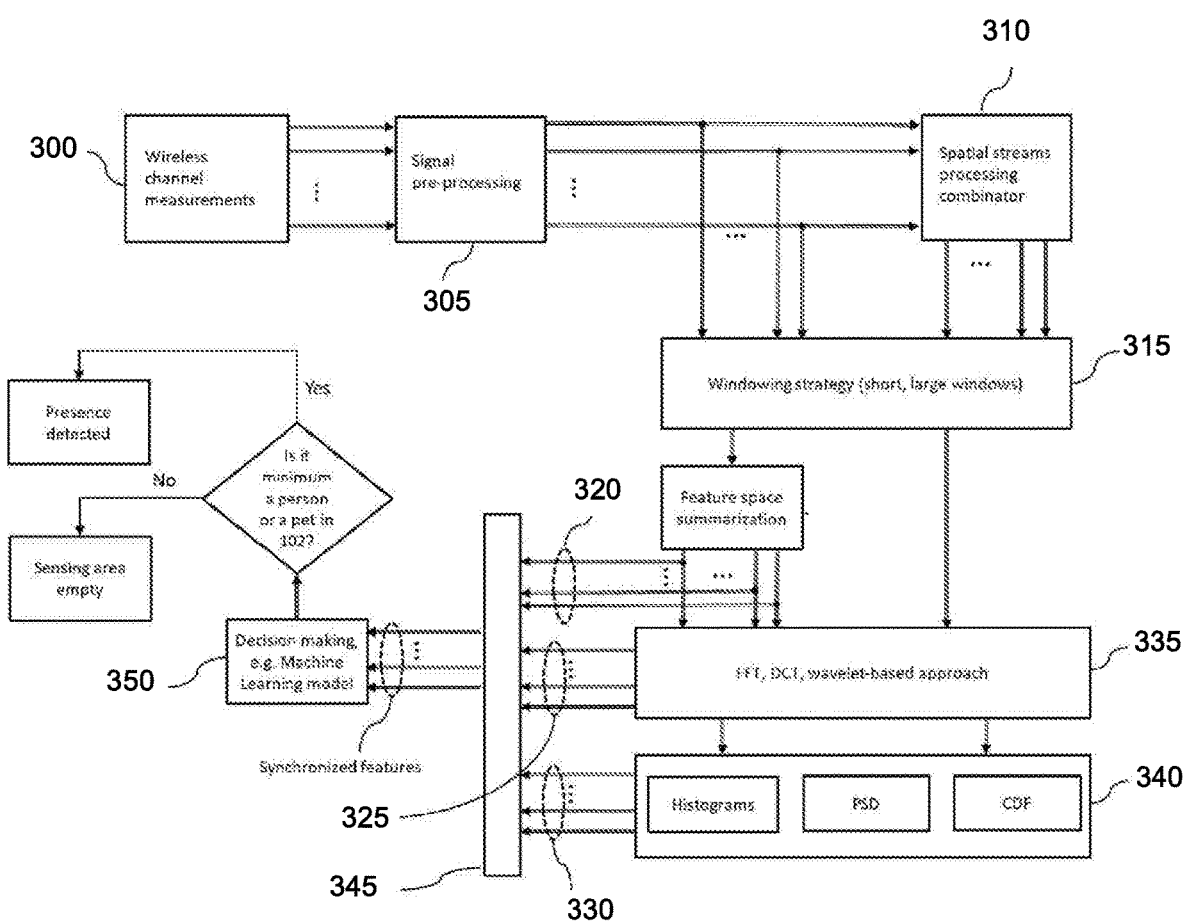
FIG. 3 is a flow diagram of the statistical-based approach proposed herein in order to detect presence through breathing rate detection.

The method analyzes flows of both magnitude and phase responses of the wireless channel between connected devices in multiple frequencies and spatial streams in MIMO channels. This is referred to as raw data or wireless channel measurements 300 in FIG. 3, which is the input into the method. A signal pre-processing module 305 is proposed right after module 300. Module 300 provides stable signals to the following modules. Some packages are discarded due to different reasons such as a defective estimation of the state of the frequency and/or impulse responses of the channel. The damaged packages are automatically detected and discarded. Module 310 is a combination of different spatial streams in MIMO systems. As an example, the phase difference between two different spatial streams for all the available subcarriers or frequency components is computed and transferred to module 315. Module 315 performs a windowing strategy to analyze data either in real-time by using short window sizes, (e.g., 128 time samples (n) for all available subcarriers or frequency components), or by using large sizes of windows for analysis of the average breathing rate, (e.g., more than 4,096 samples in a sampled signals captured with sampling rate range of 10 Hz to 100 Hz). Module 315 can receive time domain series directly from the module 305, having access to stable time series without any combination of spatial streams applied to the time series.

Some examples of dimensionality of the time series, several captures were obtained containing wireless channel measurements 300 with 1,392 vectors (here named components) of CSI time series, from 58 subcarriers for each of 24 antenna phase differences while Ntx=4 and Nrx=4.

One of the outputs of module 315 is used in a first feature set referred to as level 1. This level 1 will provide features directly taken from the windowing strategy implemented in module 315 and will be summarized as time domain features to the bus of features 345, which is in charge of synchronizing all the features that were extracted at the different levels 1, 2 and 3, corresponding to the modules 320, 325, and 330, respectively. The second output of module 315 is an input to the domain conversion module 335. In module 335, conversion from time-domain signals or time series into a different domain is performed. Some transformations performed in module 335 are, but not limited to, a discrete fourier transform (DFT), using the fast fourier transform (FFT) for example, or a discrete cosine transform (DCT), or any other transform related to frequency domain, or any wavelet transformation. In wavelet transform, the signal is decomposed in terms of some time-limited basic functions that have two degrees of freedom: scale (like frequency in sin function) which determines how compressed/stretchered the basic function is, and shift, which determines the pace where the basic function stands. Those basic functions are time-limited and there is a wide choice of basic functions for correlating with breathing measurements. The similarity between the basic function of wavelet transform and breathing signal facilitates a better extraction of breathing components from the signal.

Any of the above-mentioned mathematical transforms are applied for each time series provided through module 315 or a subset of components provided by the module 315. Only frequencies between 0.17 Hz and 0.70 Hz are considered in subsequent processing since these range covers the limits of human breathing rates. Module 335 creates inputs to the bus of features 345 and also to the module 340 that performs statistical analysis from the transformations performed in processing module 335. The statistical processing module 340 can perform any statistical summary on the input series data, either processing independent components or summarizing those independent component statistics that are parallel data series in the domain in which the data series were yielded to processing module 340. Some of those statistical analyses or summaries are histograms, power spectrum density (PSD) analysis, cumulative distribution function (CDF) and/or the probability density function (PDF). Processing module 340 then generates statistics that are used as statistical features of level 3 (330). At the decision making module 350, the question regarding whether or not there is user presence shall be answered.

All the features that were synchronized in the features bus 345 are used by decision making module 350 in decision making tasks that can use unsupervised or supervised machine learning models.

The decision making module 350 aim to use features generated in features bus 345 and build a mathematical model that automatically distinguishes between the baseline condition where no user related motion or micro motion is detected and the breathing condition where at least one user is present. Two different strategies were employed to make this binary decision, which could be categorized into unsupervised and supervised models based on the validation method.

In unsupervised approach only the features extracted from CSI data is used to build mathematical models. Some of those techniques include but not limited to distance-based clustering such as Gaussian mixture models (GMM), density-based clustering such as DBSCAN, centroid-based clustering such as kmeans and kmedians clustering, hierarchical clustering such as Agglomerative clustering, and Bayesian clustering algorithm such as latent dirichlet allocation (LDA) and hierarchical dirichlet processes (HDP). An example of such unsupervised methods that was applied in decision making module 350 is kmeans clustering, wherein a distance metric is defined between all the data points and then the whole observations is categorized into sub-groups based on the distance to the centroid of breathing condition and baseline condition.

In supervised approach, in addition to features extracted from CSI data, for a small portion of observation data, the corresponding ground truth obtained during the validation process is also used to build the mathematical models of baseline and breathing conditions. Some of those linear and non-linear supervised techniques include but not limited to, support vector machines (SVM), decision trees, k-nearest neighbor (KNN) classification, naïve bayes (NB), and deep neural networks (DNN). An example of such classification method that was applied in decision making module 350 is an SVM classifier with radial basis function (RBF) kernel that, based on some initial training from labelled data, builds the general model for classifying breathing and baseline conditions.

Figure 4:
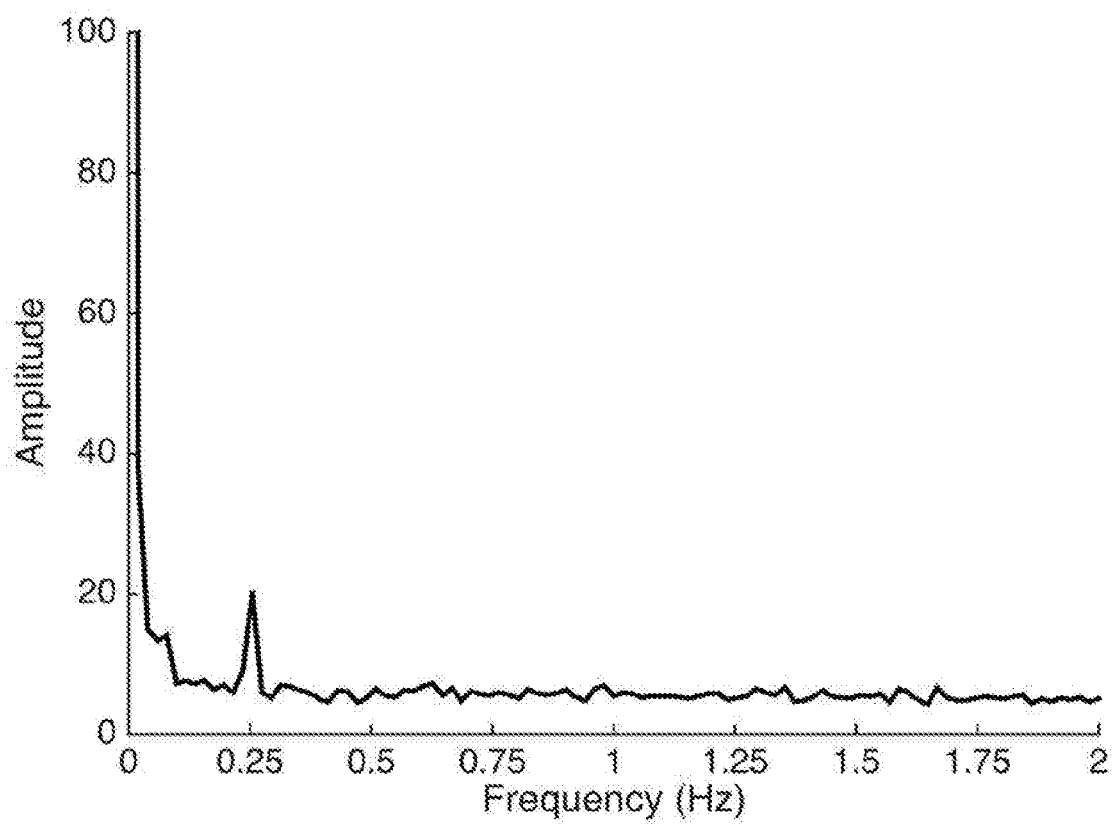
FIG. 4 is an example of the spectrum obtained from the measured wireless signal.

As an example, a simple approach is to select the frequency component exhibiting a peak which can be considered as a bin that will potentially correspond to the user's breathing rate as illustrated in FIG. 4. For each component, the frequency that yielded the maximum amplitude in the FFT output can be selected.

Figure 5:
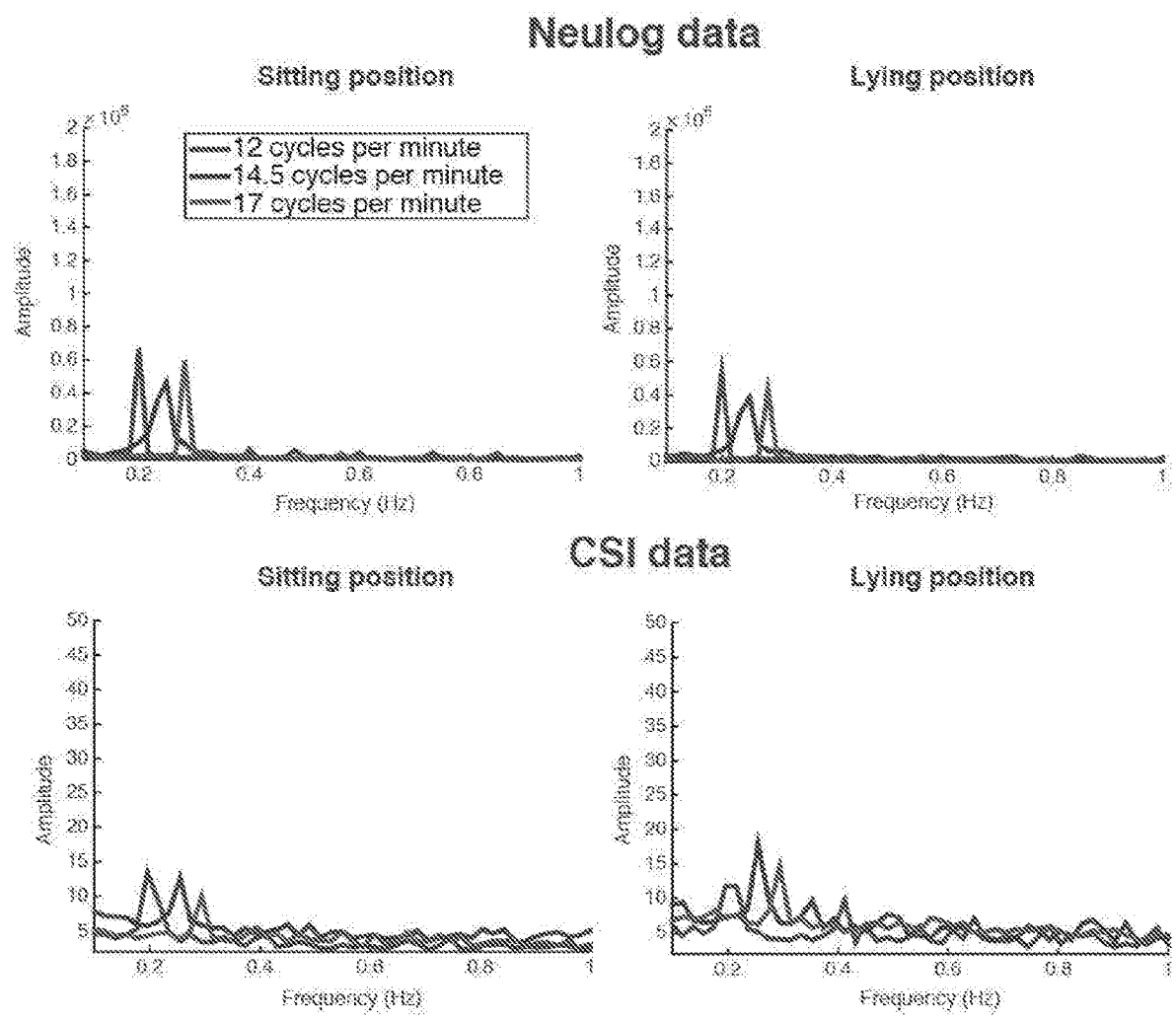
FIG. 5 is an example of the ground truth data employed to validate the method proposed herein and the spectrum summarized from the measured wireless signals used for the breathing rate estimation.

As an example, tests were performed and the following pipeline was applied to wireless channel measurements for which the breathing rate was derived from a NEULOG respiration monitor logger sensor. The sensor is connected to a monitor belt that is attached to the user's ribcage, and records variations in air pressure from the belt at 50 samples per second. CSI and NEULOG data were collected simultaneously during more than 10 captures of one minute each, per each of the locations 200, 210, 230, 240, and 250 as illustrated in FIG. 2. Captures for different breathing rate, mixed breathing rate were collected and positions such as sitting and lying were used during the validation phase. Estimated rates from CSI data, using the procedure described above, were very close to rates estimated from NEULOG data, with errors below 0.012 Hz (0.72 breathing cycle per minute) and a mean error of 0.0066 Hz (0.40 breathing cycle per minute) over the measured captures, confirming the adequacy of the procedure to estimate breathing rates from CSI. Fourier transforms for NEULOG and CSI data are presented in FIG. 5.

Figure 6:
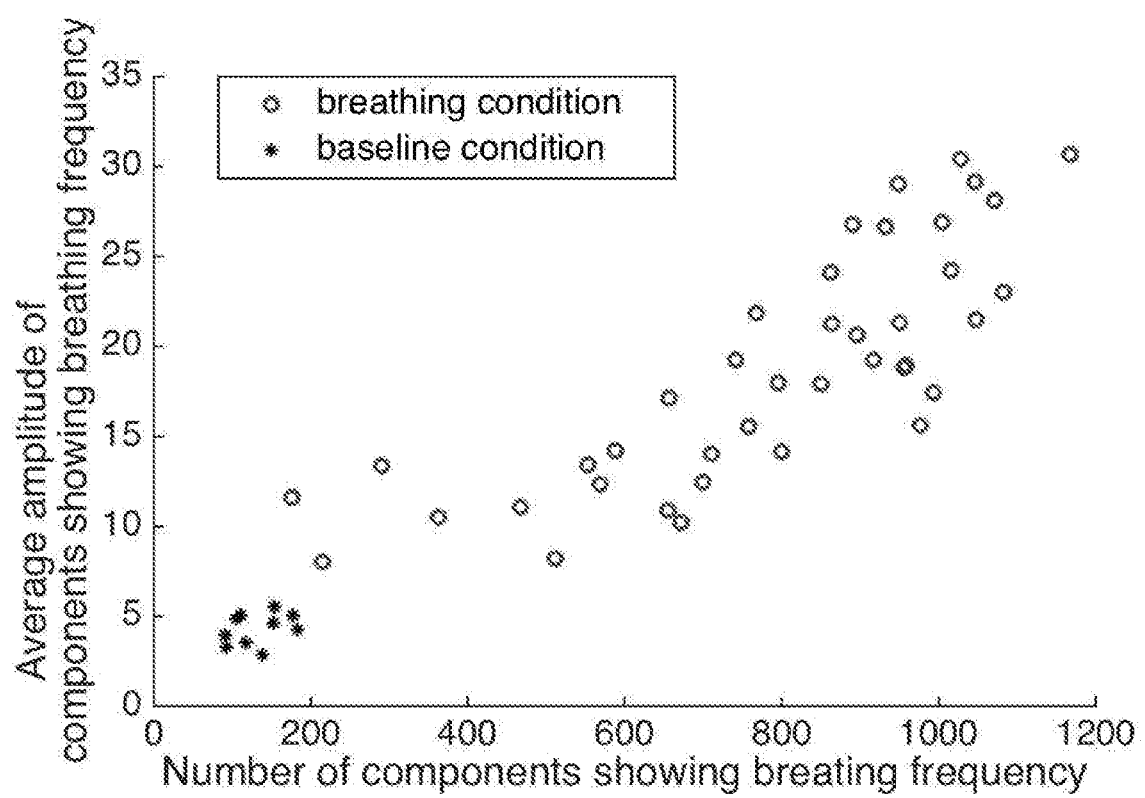
FIG. 6 illustrates an example of the feature space generated with the proposed method.

The procedure described above was applied to compare CSI data in the breathing and in the baseline conditions. Two features were extracted from each capture: the number of components with an amplitude peak that matched the most frequent one (over 1392 components), and the average amplitude of these peaks for the selected components only. As can be seen in FIG. 6, captures for the breathing and baseline conditions can be distinguished using the method proposed herein.

Figure 7:
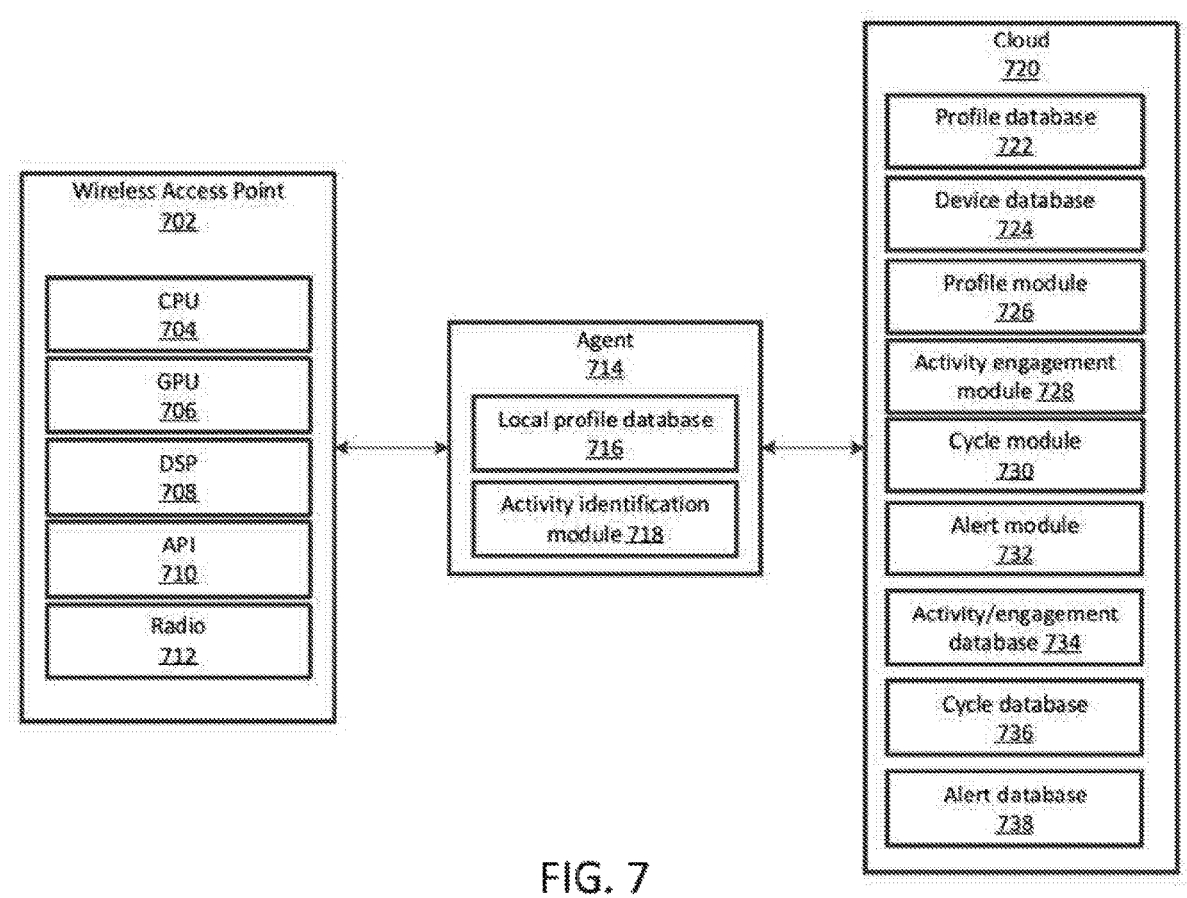
FIG. 7 illustrates a Wi-Fi motion detection system.

FIG. 7 illustrates components of the system. The wireless access point 702 is a Wi-Fi access point. The Wi-Fi access point includes but not limited to an IEEE 802.11ac or 802.11n or above access points. The wireless transceiver of the wireless access point 702 is in communication with the further stationary device over a corresponding further one of the at least one radio frequency communication link. The wireless access point 702 is configured to record a further channel state information data set for the further one of the at least one radio frequency communication link at a corresponding time. In an embodiment, the determining the activity of the user in the environment includes determining the activity of the user in the environment based on a comparison of the further channel state information data set to each of the at least one channel state information profile of each of the plurality of activity profiles. In an embodiment, the activity is determined based on a sum of a similarity measurement of the channel state information data set and a similarity measurement of the further channel state information data set. A central processing unit (CPU) 704 is the electronic circuitry within a computer that carries out the instructions of a computer program by performing the basic arithmetic, logic, controlling and input/output (I/O) operations specified by the instructions. A graphics processing unit (GPU) 706 is a specialized electronic circuit designed to rapidly manipulate and alter memory to accelerate the creation of images in a frame buffer intended for output to a display device. GPUs 706 are used in embedded systems, mobile phones, personal computers, workstations, and game consoles. Modern GPUs manipulate computer graphics and image processing and are used for algorithms that process large blocks of data in parallel. A digital signal processor (DSP) 708 is a specialized microprocessor (or a SIP block), with its architecture optimized for the operational needs of digital signal processing. The DSP 708 measures, filters or compresses continuous real-world analog signals. An application program interface (API) 710 is a set of routines, protocols, and tools for building software applications. The API 710 specifies how software components should interact. Additionally, APIs 710 are used when programming graphical user interface (GUI) components. The API 710 provides access to the channel state data to the agent 714. An access point compliant with either 802.11ac or 802.11n or above access point, allow a device to have multiple radio 712 antennas. Multiple radio 712 antennas enable the equipment to focus on the far end device, reducing interference in other directions, and giving a stronger useful signal. This greatly increases range and network speed without exceeding the legal power limits.

An agent 714 is configured to collect data from the Wi-Fi chipset, filter the incoming data then feed and pass the data to the cloud 720 for activity identification. Depending on the configuration, the activity identification can be done on the edge, at the agent level, or in the cloud, or some combination of the two. A local profile database 716 is utilized when at least a portion of the activity identification is done on the edge. This could be a simple motion/no-motion determination profile, or a plurality of profiles for identifying activities, objects, individuals, biometrics, etc. An activity identification module 718 distinguishes between walking activities and in-place activities. In general, a walking activity causes significant pattern changes of the impulse or frequency response of a channel over time for both amplitude and phase, since walking involves significant body movements and location changes. In contrast, an in-place activity (such as watching TV on a sofa) only involves relative smaller body movements that will be captured through small distortions on magnitude and/or phase of CSI.

A cloud 720 analyzes and creates profiles describing various activities. A profile database 722 is utilized when at least a portion of the activity identification is done in the cloud 720. This could be a simple motion/no-motion determination profile, or a plurality of profiles for identifying activities, objects, individuals, biometrics, etc. A device database 724 that stores the device ID of all connected wireless access points. A profile module 726 monitors the data set resulting from continuous monitoring of a target environment, to identify multiple similar instances of an activity without a matching profile in such a data set, combine that data with user feedback to label the resulting clusters to define new profiles that are then added to the profile database 722.

An activity engagement module 728 monitors the output of the activity identification module 718 in order to populate the activity/engagement database 734 with the user activity level (such as pulse or respiration rate) and engagement level (such as the amount of time the user spends watching a TV program, reading a book, engaged in conversation, etc.) over time. A cycle module 730 performs linear operations on (convolution correlation) the data (graphs) of activity levels against the data (graphs) of engagement levels (relaxation/TV, thinking/reading, etc.) for different time periods from the data in the activity/engagement database 734. For example, the patterns over the course of a week or every day or every Monday, in order to identify at what cycle length there are noticeable patterns for the correlation between activity level and engagement level.

An alert module 732 compares the current activity and engagement levels to the cycles identified by the cycle module 730. When the user deviates from the identified cycles, the alert score of the user may be affected. For example, a user has a pattern of being engaged with the TV every Sunday afternoon, and that engagement is correlated with increased respiration rate. The alert module 732 may see that there is an identified cycle for the current time on Sunday afternoon, determine if the user is engaged (e.g., watching TV) and if the activity level (e.g., respiration rate) is what may be expected based upon the identified cycle, and when there is a deviation add points to an alert score. This is done because a single variation from a pattern of behavior does not necessarily indicate an issue, but a series of deviations from identified patterns put together cumulatively is cause for concern when any one of the individual incidents may not prompt an alert from current monitoring systems. The activity/engagement database 734 stores the activity level of the observed user (such as respiration rate, pulse rate, etc.) along with the user level of intellectual or emotion engagement (such as watching TV, reading a book, engaged in conversation, etc.) over time. A cycle database 736 store the cycles identified by the cycle module. Cycles are time periods over which the same pattern of engagement and activity level are shown to repeat. An alert database 738 stores the current alert score of the user being observed along with the rules for who to contact in the event the observed user alert score exceeds a defined threshold(s). The alert database 738 contains the user current alert score, as calculated by the alert module 732, and the actions that need to be taken based upon the current alert score. Table 1 (provided below) illustrates an exemplary alert database 738.

TABLE 1

| Current Alert Score | 1.5 |
|---|---|
| Alert Score | Action |
| >2 | Send report to caregiver; send IOT message to confirm condition of user |
| >3 | Send alert to caregiver |

Figure 8:
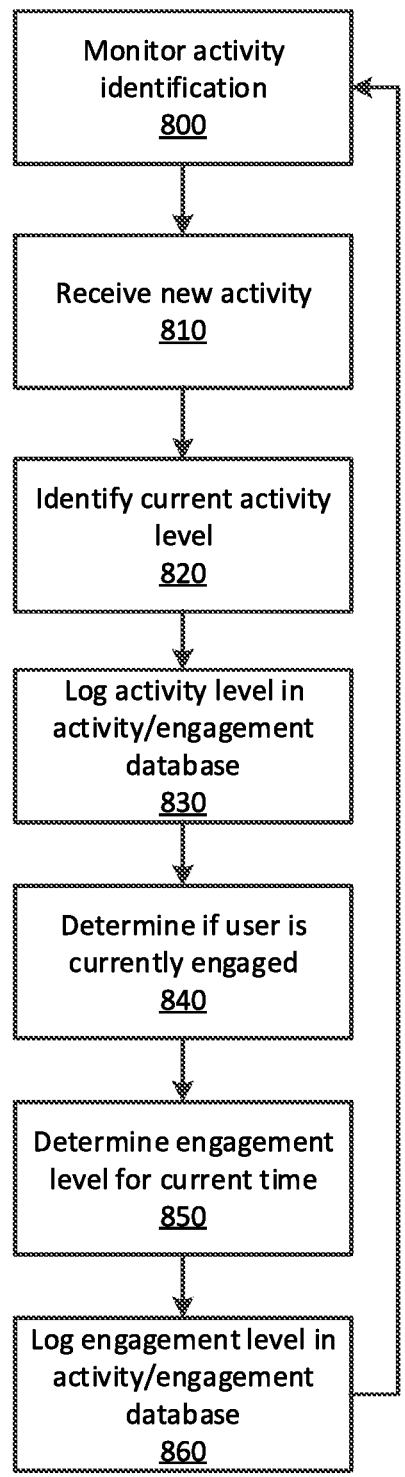
FIG. 8 illustrates an activity engagement module.

Functioning of the activity engagement module 728 is explained with reference to FIG. 8. The activity engagement module may constantly be monitoring the activity identification module 718 for new identified activities in step 800. New identified activities may be received in step 810. The current activity level (such as pulse or respiration rate) may be identified in step 820. The current activity level may be logged for this exemplary respiration rate in the activity/engagement database 734 in step 830. The activity defined by the activity identification module 718 may be used to determine if the user is currently engaged. For the purposes of this application, "engaged" may be inclusive of both emotional and intellectual engagement. Certain activities in the profile database 722 are classified as emotionally or intellectually engaging (such as watching TV, reading a book, engaging in conversation with others, etc.) in step 840. The engagement level may be determined for the current time slice. In this example, the percentage of a given time slice (e.g., five minutes) is taken and the percentage of time the user is engaged in the activity of watching TV is used as the engagement level. For example, the user was watching TV for four out of the five minutes in a time slice. The engagement level for that time slice may be identified as 80% in step 850. The current engagement level may be logged in the activity/engagement database 734. The method may return to monitoring the activity identification module 718 in step 860.

Figure 9:
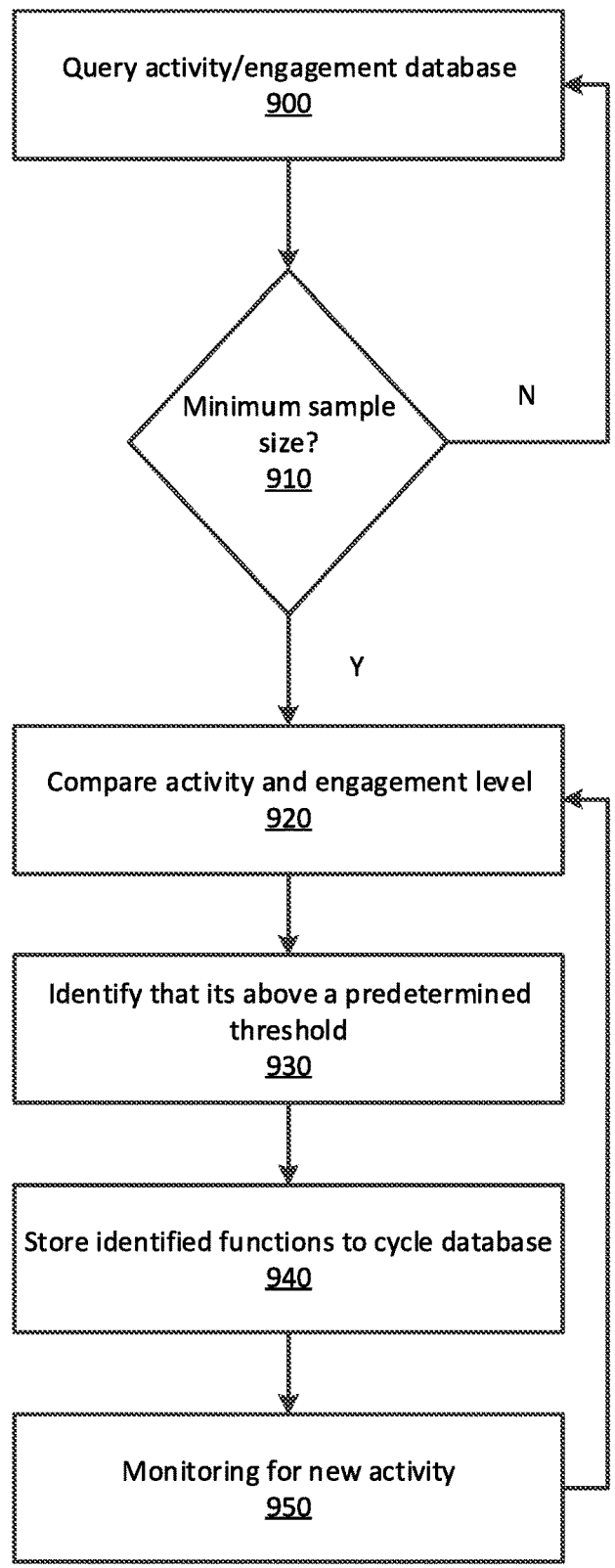
FIG. 9 illustrates a cycle module.

Functioning of the cycle module 730 is explained with reference to FIG. 9. The process begins when the system is installed, and the cycle module 730 begins querying the activity/engagement database 734 for activity data about the user, such as pulse or respiration rate, as well as emotional or intellectual engagement levels of the user, compiled over time by the activity engagement module 728 in step 900. The minimum sample size has been met to begin to identify cycles. Depending upon the application, the minimum sample size could vary widely. For example, a more immobile user may stick to a more strict routine than an independent user.

The system may need a larger sample for the more independent user who is likely to have a greater variety of activities in the routine in step 910. The activity level over time is compared against the engagement level over time for as many different time periods are feasible across the provided sample using at least one statistical means, such as convolution, linear regression, etc. For example, if the minimum sample size was one month, each week could be looked at, or each weekday, or each Monday, or from 1:00 pm to 5:00 pm every Sunday. In this fashion, cycles in the user engagement and activity patterns can be detected and used to identify when a user is breaking routine in step 920. Of the resulting functions from step 920, those that are above the predetermined threshold for statistical significance may be identified (e.g., two function convoluted against each other where the resulting function is at least 80% of a step function) in step 930. The functions identified in step 930 may be written to the cycle database 736 in step 940. The activity/engagement database 734 may be monitored for new data, and the method may return to step 920 to identify new cycles in step 950.

Figure 10:
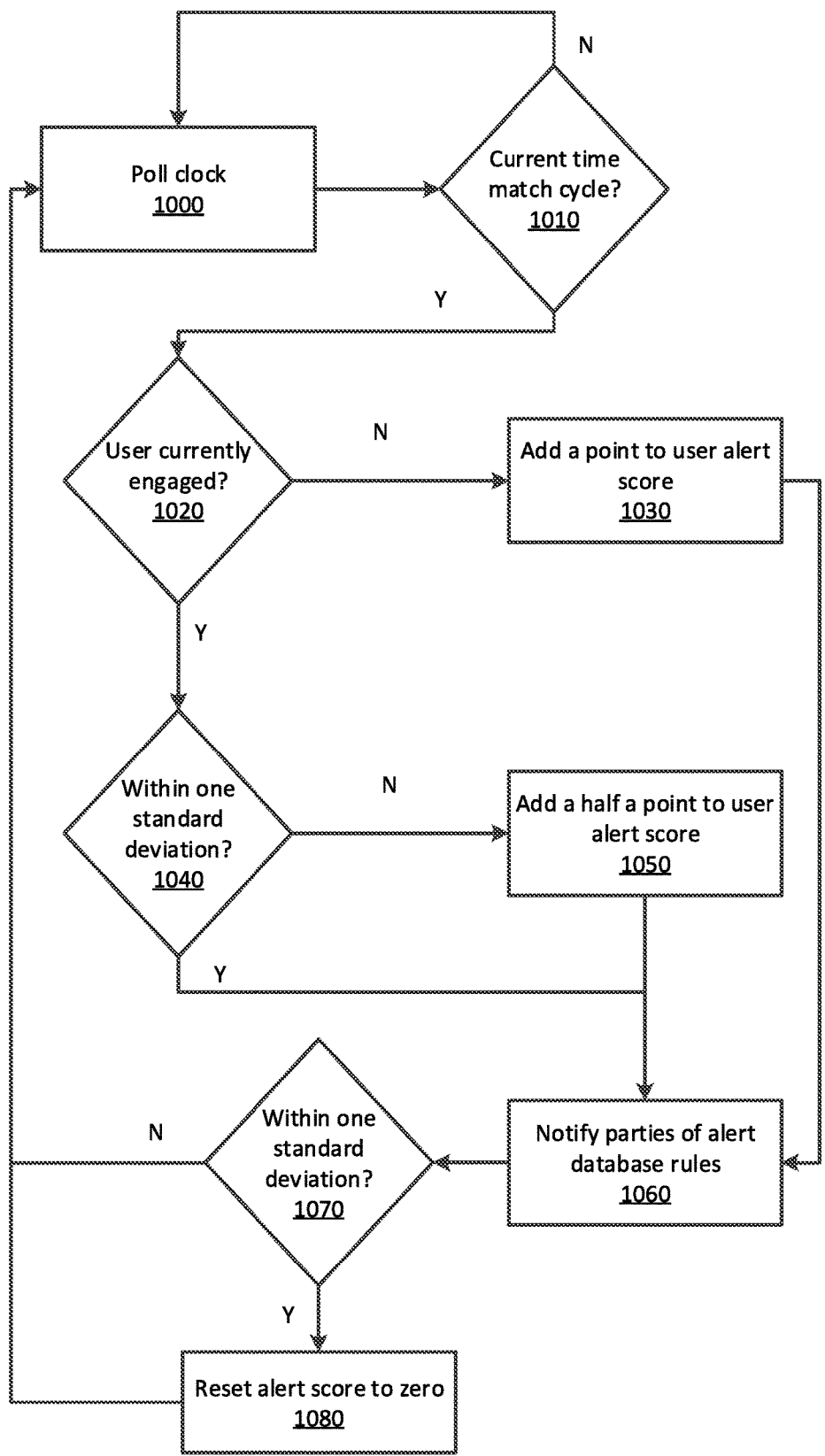
FIG. 10 illustrates an alert module.

Functioning of the alert module 732 is explained with reference to FIG. 10. The alert module 732 is constantly polling the cycle database 736 for newly identified cycles, specifically the times of the identified cycles in step 1000. The alert module 732 polls the system's internal clock to determine the time. The current time may be compared to the time windows of all identified cycles in the cycle database 736. The method may return to polling the clock if the current time does not match in step 1010. If the current time does match an identified cycle, the user is currently engaged (e.g., watching TV) as was expected by the cycle in step 1020. If the user is not engaged as expected, one may be added to the user alert score in the alert database 738 in step 1030. If the user is engaged as expected, the user activity level (e.g., respiration rate) is within one standard deviation of the respiration rate expected by the cycle in step 1040. If the user activity level is outside of the expected range, 0.5 may be added to the user alert score in the alert database 738 in step 1050. Parties may be notified per the rules in the alert database 738 based upon the user current alert score. For example, the user may not be engaged in the first observed cycle (adding one to the user's alert score), but the user was engaged in the second cycle with a respiration rate that was lower than normally seen in the identified cycle (adding 0.5 to the alert score), while the third cycle shows the user was again not engaged (adding one to the alert score). This brings the exemplary user alert score over the first threshold of 2 in the alert database. The third time being off-cycle may trigger a report to be sent to designated recipients (e.g., caregiver(s) of the user) indicating that the user is deviating from the routines. Optionally, a message may be sent to the recipient via an IoT device in the home to check on the subject user. During the fourth cycle, the user may be engaged, but again have a respiratory rate below the expected level (adding 0.5 to the alert score) and triggering the second threshold of responses in the alert database 738. An alert may be sent to the caregiver(s) in step 1060. In step 1070, the alert module 732 determines if the user alert score has reached 3. Once the alert score has reached 3 (or other chosen threshold for caregiver intervention), the alert score is reset to 0 at step 1080.

One skilled in the art may appreciate that, for the processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for detecting a user, the method comprising:
generating a baseline condition based on one or more captures by one or more connected devices in a sensing area when the user is not present in the sensing area;
receiving activity data and engagement level data associated with the user from the one or more connected devices in the sensing area, wherein a channel frequency response between the one or more connected devices indicates a breathing condition associated with the user;
storing the activity data and the engagement level data for a plurality of time periods;
identifying one or more time periods in the plurality of time periods where the stored user activity data and the stored engagement level data are correlated;
comparing current activity data and current engagement level data to identify one or more cycles, wherein the identified cycles correspond to one or more time periods where the activity data and the engagement level data repeat;
detecting a deviation in the current activity data from the identified cycles;
incrementing an alert score associated with the user;
determining the alert score is above a predefined threshold; and
sending an alert to a device associated with the user.

2. The method of claim 1, further comprising detecting spectral components in a micro motion frequency range in the sensing area.

3. The method of claim 1, further comprising detecting a breathing rate of the user based on analyzing information about the channel frequency response between the one or more connected devices.

4. The method of claim 3, further comprising comparing the baseline condition with the breathing condition to determine that the breathing condition indicates that the user is present in the sensing area.

5. The method of claim 1, wherein the activity data further indicates a pulse rate or a respiration rate of the user.

6. The method of claim 1, wherein the engagement level data includes an amount of time the user spends watching TV, reading, or engaging in a conversation.

7. The method of claim 1, further comprising resetting the alert score to zero.

8. The method of claim 1, wherein the identified cycles are based on a minimum sample time period.

9. A system for detecting a user, the system comprising:
one or more connected devices located in a sensing area; and
a cloud server that:
generates a baseline condition based on one or more captures by the one or more connected devices when the user is not present in the sensing area;
receives activity data and engagement level data associated with the user from the one or more connected devices, wherein a channel frequency response between the one or more connected devices indicates a breathing condition associated with the user;
stores the activity data and the engagement level data for a plurality of time periods;
identifies one or more time periods in the plurality of time periods where the stored user activity data and the stored engagement level data are correlated,
compares current activity data and current engagement level data to identify one or more cycles, wherein the identified cycles correspond to one or more time periods where the activity data and the engagement level data repeat, detects a deviation in the current activity data from the identified cycles, increments an alert score associated with the user, determines the alert score is above a predefined threshold, and sends an alert to a device associated with the user.

10. The system of claim 9, wherein the cloud server further detects a breathing rate of the user based on analyzing information about the channel frequency response between the one or more connected devices.

11. The system of claim 10, wherein the cloud server further compares the baseline condition with the breathing condition to determine that the breathing condition indicates that the user is present in the sensing area.

12. The system of claim 9, wherein the activity data further indicates a pulse rate or a respiration rate of the user.

13. The system of claim 9, wherein the engagement level data includes an amount of time the user spends watching TV, reading, or engaging in a conversation.

14. The system of claim 9, further comprising resetting the alert score to zero.

15. The system of claim 9, wherein the identified cycles are based on a minimum sample time period.

16. A non-transitory, computer-readable storage medium having embodied thereon instructions executable by one or more processors to perform a method for detecting a user, the method comprising:

generating a baseline condition based on one or more captures by one or more connected devices in a sensing area when the user is not present in the sensing area;

receiving activity data and engagement level data associated with the user from the one or more connected devices in all the sensing area, wherein a channel frequency response between the one or more connected devices indicates a breathing condition associated with the user;

storing the activity data and the engagement level data for a plurality of time periods;

identifying one or more time periods in the plurality of time periods where the stored user activity data and the stored engagement level data are correlated;

comparing current activity data and current engagement level data to identify one or more cycles, wherein the identified cycles correspond to one or more time periods where the activity data and the engagement level data repeat;

detecting a deviation in the current activity data from the identified cycles;

incrementing an alert score associated with the user;

determining the alert score is above a predefined threshold; and sending an alert to a device associated with the user.

* * * * *